United States Patent [19]

Chou et al.

[11] Patent Number: 5,340,818
[45] Date of Patent: Aug. 23, 1994

[54] METHODS AND COMPOSITIONS FOR INHIBITING TUMOR CELL GROWTH

[75] Inventors: Ting-Chao Chou, New York, N.Y.; Tian-Shung Wu, Tianan, Taiwan

[73] Assignee: Sloan-Kettering Institute for Cancer Research, New York, N.Y.

[21] Appl. No.: 16,052

[22] Filed: Feb. 10, 1993

Related U.S. Application Data

[63] Continuation-in-part of Ser. No. 530,103, May 25, 1990, abandoned, which is a continuation-in-part of Ser. No. 357,323, May 25, 1989, abandoned.

[51] Int. Cl.$^5$ .................................................. A61K 31/44
[52] U.S. Cl. ........................................ 514/297; 514/290
[58] Field of Search ................. 514/290, 292, 295, 297

[56] References Cited

U.S. PATENT DOCUMENTS

| | | | |
|---|---|---|---|
| 4,626,540 | 12/1986 | Capps | 514/297 |
| 4,666,917 | 5/1987 | Wilkinson | 514/297 |
| 5,229,395 | 7/1993 | Watanabe et al. | 514/297 |

*Primary Examiner*—Marianne M. Cintins
*Assistant Examiner*—T. J. Criares
*Attorney, Agent, or Firm*—John P. White

[57] ABSTRACT

The subject invention discloses methods of inhibiting growth of tumor cells which comprise contacting the cells with a growth inhibiting amount of a compound having one of following structures:

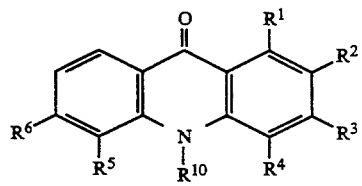

wherein $R^1$ is a hydroxyl or acetyl group; $R^2$ is hydrogen, $-CH_2-CH=C(CH_3)_2$ or a method group; $R^3$ is a hydroxyl, methoxy or acetyl group; $R^4$ is hydrogen, $-CH_2-CH=C(CH_3)_2$ or a methoxy group; $R^5$ is a hydroxyl, methoxy or acetyl group; is hydrogen or a hydroxyl, methoxy or acetyl group; and $R^{10}$ is a methyl group,

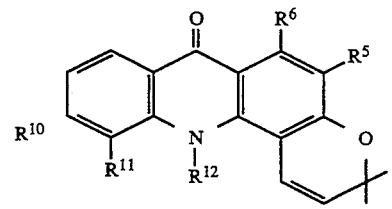

wherein $R^5$ is hydrogen or $-CH_2-CH=C(CH_3)_2$; $R^6$ is a hydroxyl group; $R^{10}$ is hydrogen or a hydroxyl group; $R^{11}$ is a hydroxyl or methoxy group; and $R^{12}$ is hydrogen or a methyl group.

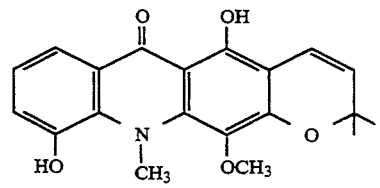

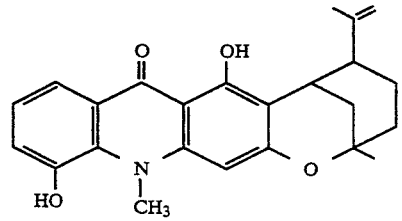

8 Claims, No Drawings

METHODS AND COMPOSITIONS FOR INHIBITING TUMOR CELL GROWTH

This application is a continuation-in-part of U.S. Ser. No. 07/530,103, filed May 25, 1990, now abandoned which is a continuation-in-part of U.S. Ser. No. 07/357,323, filed May 25, 1989, now abandoned and the contents of which are hereby incorporated by reference into the present disclosure.

The invention described herein was made in the course of work under Grant Nos. CA18856, CA27569, and AI26056 from the National Cancer Institute, U.S. Department of Health and Human Services. The U.S. Government may have certain rights in this invention.

BACKGROUND OF THE INVENTION

A number of naturally occurring acridone alkaloids have been isolated from the family Rutaceae, but only acronycine (1) has been noted for its antitumor activity. (Throughout the specification, compounds will be cross-referenced with underlined numbers to facilitate reading and to avoid repetition of long chemical names).

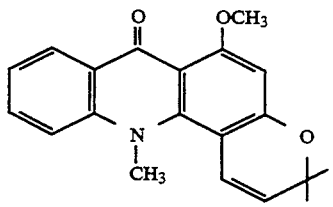

Acronycine was isolated from the bark of the Australian scrub, *Acronychi baueri Schott* (Rutaceae) (Hughes, G. K., et al., Nature, 162:223-224 (1948); McDonald, P. L. and A. V. Robertson, Aust. J. Chem., 19: 275-281 (1966); Svoboda, G. H., Lloydia, 29:206-224 (1966)). Experimental studies on acronycine in animals (Finkelstein, T. Z., et al. Cancer Chemother. Reports, 59:975-983 (1975); Schneider, J., et al., J. Med. Chem., 15:266-270 (1972); Svoboda (1966); Svoboda, G. H., et al., J. Pharm. Sci., 55:758-768 (1966); Svoboda, G. H., U.S. Pat. No. 3,985,899, issued Oct. 12, 1976; Svoboda, G. H., U.S. Pat. No. 4,309,431, issued Jan.5, 1982) showed it to be effective against a wide range of neoplasms. Because of its antitumor activity, it has undergone clinical trials (Division of Cancer Treatment. Program Statistics, Mar. 30, 1970, Department HEW, Public Health Service, NIH, IND status filed for acronycine).

Acronycine was found to inhibit the incorporation of extracellular nuclosides into the DNA and RNA of cultured L5178Y cells, but did not interact with DNA (Dunn, B. P., et al. Cancer Res., 33:2310-2319 (1973)). The inhibitory effect of the alkaloid may be the result of an alteration in the transport of uridine through the plasma membrane instead of impaired nucleoside or nucleotide phosphorylation (Dunn, B. P., et al. Cancer Res., 33:2310-2319 (1973)). Similar mechanisms of action were also observed in other studies which indicated that the alkaloid acts primarily on membranous organelles, and its delayed effects may be in part due to interference with the structure, function, and/or turnover of cell-surface components (Tan, P., and N. Auersperg, Cancer Res., 33:2320-2329 (1973)).

Several derivatives of acridinone have been synthesized and tested for their antitumor activity (Liska, K. J., J. Med. Chem., 15:1177-1179 (1972); Radzikowski, C., et al. Arch. Immunol. Ther. Exp., 19:219-228 (1971); Reisch, J. and S. M. E. Aly, Arch. Pharm., 319:25-28 (1986); Schneider, J., et al. J. Med. Chem. 15:266-270 (1972); Svoboda, G. H. Lloydia 29:206-224 (1966)). Of those derivatives synthesized, only O-(dimethylaminoethyl)noracronycine (2) (Reisch, J. and S. M. E. Aly, Arch. Pharm. 319:25-28 (1986)) and 1-nitro-$N^{10}$-substituted acridine-9-ones (3) (Radzikowski, C., et al., Arch. Immunol. Ther. Exp. 19:219-228 (1971)), showed biological activity. Compound 2, bearing a charged dimethyl-aminoethyl side-chain, was reported to exhibit significant antitumor activity (Reisch, J. and S. M. E. Aly, Arch. Pharm. 319:25-28 (1986)). It is possible, therefore, that change of the overall molecular lipophilic-hydrophilic balance and electronic distribution caused by addition of a charged side-chain or nitro function on the molecule of acridine-9-one alter biological activity.

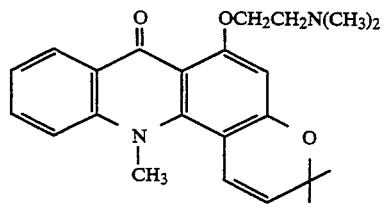

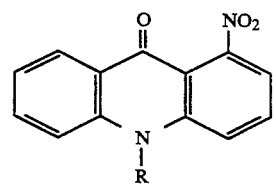

Svoboda, G. H., U.S. Pat. Nos. 4,309,431 and 3,985,899, filed Jan. 5, 1982 and Oct. 12, 1976, respectively, teach a method of inhibiting growth of tumor cells using acronycine. However, they do not teach or suggest that other acridone alkaloids may be used to inhibit tumor growth.

To determine structure-activity relationships, the effects of 50 acridone alkaloids on the incorporation of the labeled precursors, [$^3$H-methyl]dThd, [5-$^3$H]Cyd and [2,3,4,5-$^3$H)L-Leu, into DNA, RNA and protein, respectively, were studied. The inhibition by these acridone alkaloids against human leukemic HL-60 cell growth was also studied.

SUMMARY OF THE INVENTION

The subject invention discloses a method of inhibiting growth of tumor cells which comprises contacting the cells with a growth inhibiting amount of a compound having the structure:

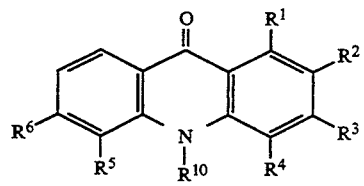

wherein $R^1$ is a hydroxyl or acetyl group; $R^2$ is hydrogen, —CH$_2$—CH═C(CH$_3$)$_2$ or a methoxy group; $R^3$ is a hydroxyl, methoxy or acetyl group; $R^4$ is hydrogen, —CH₂—CH=C(CH₃)₂ or a methoxy group; R⁵ is a hydroxyl, methoxy or acetyl group; R⁶ is hydrogen or a hydroxyl, methoxy or acetyl group; and R¹⁰ is a methyl group.

A composition for inhibiting growth of tumor cells comprising an amount of the above-identified structure effective to inhibit growth of tumor cells and a physiologically acceptable carrier is also provided.

This invention also provides a method of inhibiting growth of tumor cells which comprises contacting the cells with a growth inhibiting amount of a compound having the structure:

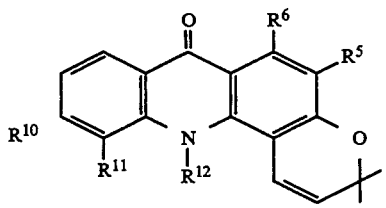

wherein R⁵ is hydrogen or —CH₂—CH=C(CH₃)₂; R⁶ is a hydroxyl group; R¹⁰ is hydrogen or a hydroxyl group; R¹¹ is a hydroxyl or methoxy group; and R¹² is hydrogen or a methyl group.

A composition for inhibiting growth of tumor cells comprising an amount of the above-identified structure effective to inhibit growth of tumor cells and a physiologically acceptable carrier is also provided.

The subject invention also discloses a method of inhibiting growth of tumor cells which comprises contacting the cells with a growth inhibiting amount of a compound having the structure:

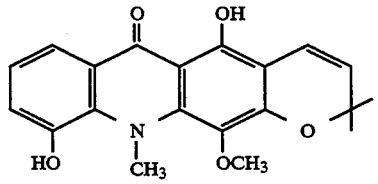

Further provided is a composition comprising an amount of the above-identified compound effective to inhibit growth of tumor cells and a physiologically acceptable carrier.

The subject invention additionally discloses a method of inhibiting growth of tumor cells which comprises contacting the cells with a growth inhibiting amount of a compound having the structure:

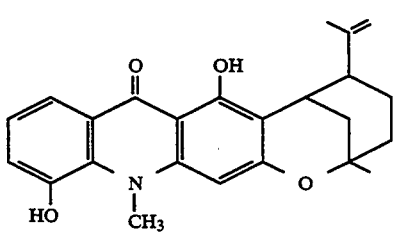

Further provided is a composition comprising an amount of the above-identified compound effective to inhibit growth of tumor cells and a physiologically acceptable carrier.

The subject invention provides a method of inhibiting growth of leukemia cells in a host in need of treatment therefor which comprises administering to the host an amount of a compound having the structure:

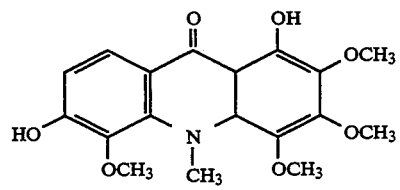

effective to inhibit growth of the leukemia cells.

The invention also provides a composition for inhibiting growth of leukemia cells in a host in need of treatment thereof which comprises an amount of the compound having the structure:

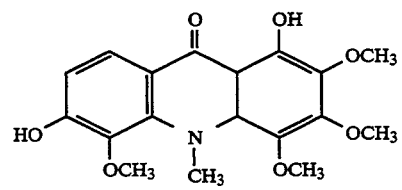

effective to inhibit growth of leukemia cells and a physiologically acceptable carrier.

The invention also provides a composition for inhibiting growth of solid tumors in a host in need of treatment thereof which comprises an amount of the compound having the structure:

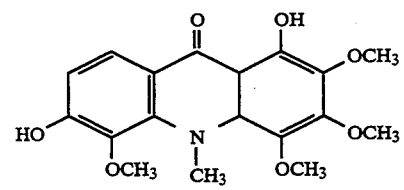

effective to inhibit growth of solid tumors and a physiologically acceptable carrier.

DETAILED DESCRIPTION OF THE INVENTION

The subject invention discloses a method of inhibiting growth of tumor cells which comprises contacting the cells with a growth inhibiting amount of a compound having the structure:

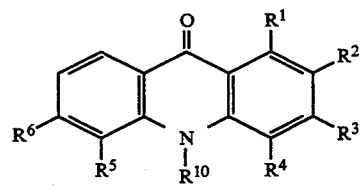

wherein R¹ is a hydroxyl or acetyl group; R² is hydrogen, —CH₂—CH=C(CH₃)₂ or a methoxy gruop; R³ is a hydroxyl, methoxy or acetyl group; R⁴ is hydrogen, —CH₂—CH=C(CH₃)₂ or a methoxy group; R⁵ is a hydroxyl, methoxy or acetyl group; R⁶ is hydrogen or a hydroxyl, methoxy or acetyl group; and R¹⁰ is a methyl group.

All methods disclosed in this application may be effected in vitro or in vivo. When these methods are performed in vivo, the administration of the compound may be effected by any of the well known methods, including but not limited to oral, intravenous, intramuscular, and subcutaneous. The method of delivery, the amount to be used, and the frequency of delivery are expected to vary according to the situations, the carrier used, and result desired. However, those variables are readily determinable by one skilled in the art.

In one compound of the preferred embodiment, $R^1$ is an acetyl group; $R^2$ is hydrogen; $R^3$ is a methoxy group; $R^4$ is —CH$_2$—CH=C(CH$_3$)$_2$; $R^5$ is an acetyl group; and $R^6$ is hydrogen. This compound is O,O-diacetyl-glycocitrine-I (14).

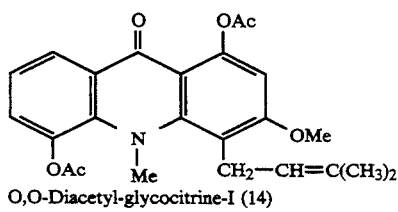
O,O-Diacetyl-glycocitrine-I (14)

In the first subgroup of the preferred embodiment, $R^1$ is a hydroxyl group and $R^5$ is a hydroxyl or a methoxy group.

In one preferred compound of the first subgroup, $R^2$ is hydrogen; $R^3$ is a methoxy group; $R^4$ is a methoxy group; $R^5$ is a hydroxyl group; and $R^6$ is hydrogen. This compound is citrusinine-I (16)

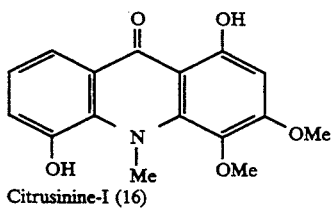
Citrusinine-I (16)

In another preferred compound of this subgroup, $R^2$ is —CH$_2$—CH=C(CH$_3$)$_2$; $R^3$ is a hydroxyl group; $R^4$ is hydrogen; $R^5$ is a methoxy group; and $R^6$ is a hydroxyl group. This compound is buntanine (25).

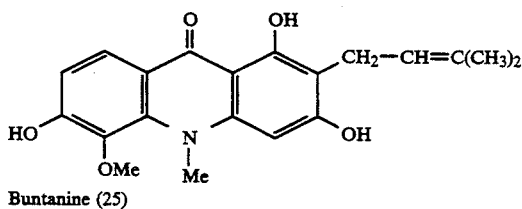
Buntanine (25)

The first subgroup may be further divided to a second subgroup wherein $R^4$ is —CH$_2$—CH=C(CH$_3$)$_2$ or a methoxy group.

In one preferred compound of this second subgroup, $R^2$ is —CH$_2$—CH=C(CH$_3$)$_2$; $R^3$ is a hydroxyl group; $R^4$ is —CH$_2$—CH=C(CH$_3$)$_2$; $R^5$ is a hydroxyl group; and $R^6$ is hydrogen. This compound is N-methyl-atalaphylline (26).

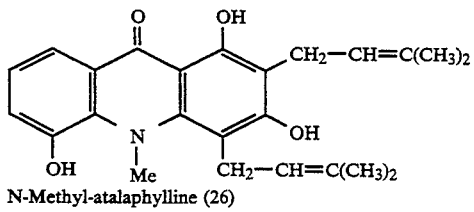
N-Methyl-atalaphylline (26)

The second subgroup may be further divided to a third subgroup wherein $R^2$ is hydrogen or a methoxy group; and $R^3$ is a methoxy or acetyl group.

In one preferred compound of this subgroup, $R^2$, $R^3$, $R^4$ and $R^5$ are methoxy groups; and $R^6$ is a hydroxyl group. This compound is glyfoline (31):

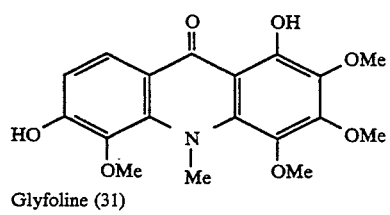
Glyfoline (31)

The third subgroup may be further divided to a fourth subgroup wherein $R^2$ is hydrogen.

In one preferred compound of this subgroup, $R^3$ is a methoxy group; $R^4$ is —CH$_2$—CH=C(CH$_3$)$_2$; $R^5$ is a hydroxyl group; and $R^6$ is hydrogen. This compound is glycocitrine-I (13).

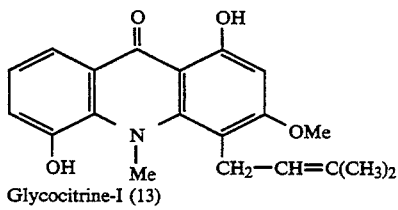
Glycocitrine-I (13)

The fourth subgroup maybe further divided to a fifth subgroup, wherein $R^5$ is a methoxy group.

In one preferred compound of this subgroup, $R^3$ is methoxy group; $R^4$ is a methoxy group; and $R^6$ is hydrogen. This compound is 5-O-methyl-citrusinine-I (17):

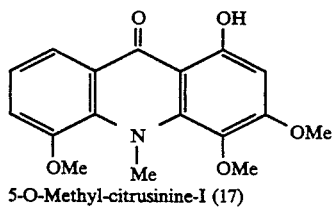
5-O-Methyl-citrusinine-I (17)

The fifth subgroup maybe further divided to a sixth subgroup, wherein $R^4$ is —CH$_2$—CH=C(CH$_3$)$_2$; and $R^6$ is a hydroxyl, methoxy or acetyl group.

In one preferred compound of this subgroup, $R^3$ and $R^6$ are methoxy groups. This compound is grandisinine (29):

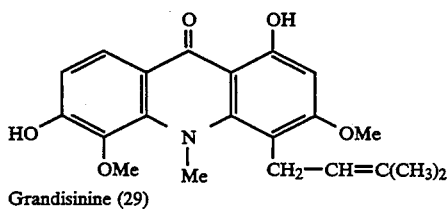
Grandisinine (29)

The sixth subgroup maybe further divided to a seventh subgroup, wherein $R^6$ is a methoxy or acetyl group.

In one preferred compound of this subgroup, $R^3$ is an acetyl group and $R^4$ is a methoxy group. This compound is 3,6-O,O-diacetyl-prenylcitpressine (28):

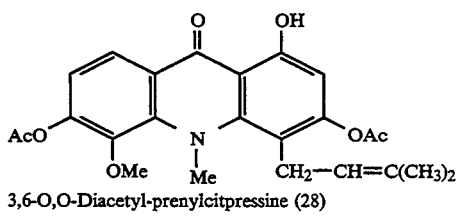
3,6-O,O-Diacetyl-prenylcitpressine (28)

In another preferred compound of this subgroup, $R^3$ and $R^4$ are methoxy groups. This compound is balyumine-B (30):

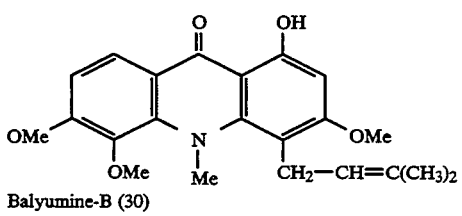
Balyumine-B (30)

The subject invention also provides a composition for inhibiting growth of tumor cells which comprises an amount of the compound having the structure:

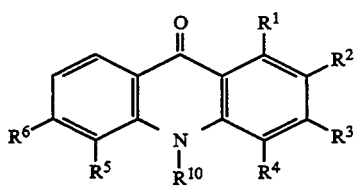

wherein $R^1$ is a hydroxyl or acetyl group; $R^2$ is hydrogen, —CH$_2$—CH=C(CH$_3$)$_2$ or a methoxy group; $R^3$ is a hydroxyl, methoxy or acetyl group; $R^4$ is hydrogen, —CH$_2$—CH=C(CH$_3$)$_2$ or a methoxy group; $R^5$ is a hydroxyl, methoxy or acetyl group; $R^6$ is hydrogen or a hydroxyl, methoxy or acetyl group; and $R^{10}$ is a methyl group; effective to inhibit growth of tumor cells and a physiologically acceptable carrier.

This invention also provides for the above-indicated compositions wherein the compound comprises hydrophilic substituents to increase solubility. Hydrophilic molecules which may be used as substituents are well known in the art. However, compositions comprising the disclosed compounds with hydrophilic substituents are previously unknown.

In one compound of the preferred embodiment, $R^1$ is an acetyl group; $R^5$ is hydrogen; $R^3$ is a methoxy group; $R^4$ is —CH$_2$—CH=C(CH$_3$)$_2$; $R^5$ is an acetyl group; and $R^6$ is hydrogen. This compound is O,O-diacetyl-glycocitrine-I (14):

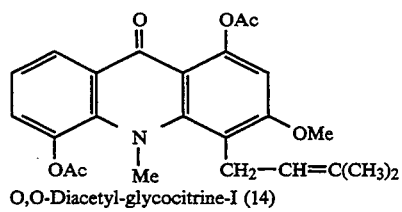
O,O-Diacetyl-glycocitrine-I (14)

In the first subgroup of the preferred embodiment, $R^1$ is a hydroxyl group and $R^5$ is a hydroxyl or a methoxy group.

In one preferred compound of the first subgroup, $R^2$ is hydrogen; $R^3$ is a methoxy group; $R^4$ is a methoxy group; $R^5$ is a hydroxyl group; and $R^6$ is hydrogen. This compound is citrusinine-I (16):

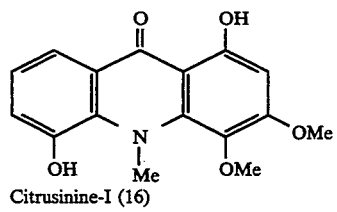
Citrusinine-I (16)

In another preferred compound of this subgroup, $R^2$ is —CH$_2$—CH=C(CH$_3$)$_2$; $R^3$ is a hydroxyl group; $R^4$ is hydrogen; $R^5$ is a methoxy group; and $R^6$ is a hydroxyl group. This compound is buntanine (25):

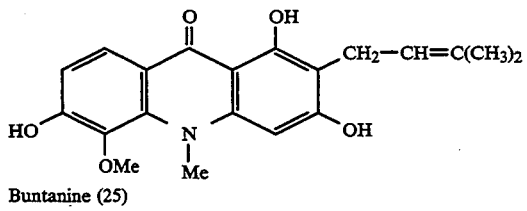
Buntanine (25)

The first subgroup may be further divided to a second subgroup, wherein $R^4$ is —CH$_2$—CH=C(CH$_3$)$_2$ or a methoxy group.

In one preferred compound of this second subgroup, $R^2$ is —CH$_2$—CH=C(CH$_3$)$_2$; $R^3$ is a hydroxyl group; $R^4$ is —CH$_2$—CH=C(CH$_3$)$_2$; $R^5$ is a hydroxyl group; and $R^6$ is a hydrogen. This compound is N-methyl-atalaphylline (26):

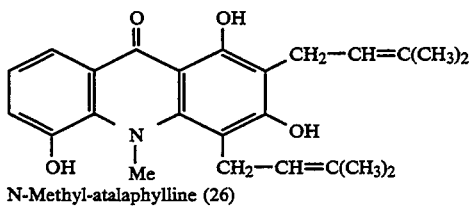
N-Methyl-atalaphylline (26)

The second subgroup maybe further divided to a third subgroup, wherein $R^2$ is hydrogen or a methoxy group; and $R^3$ is a methoxy or acetyl group.

In one preferred compound of this subgroup, $R^2$, $R^3$, $R^4$ and $R^5$ are methoxy groups; and $R^6$ is a hydroxyl group. This compound is glyfoline (31):

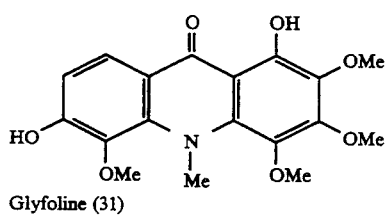
Glyfoline (31)

The third subgroup maybe further divided to a fourth subgroup wherein $R^2$ is hydrogen.

In one preferred compound of this subgroup, $R^3$ is a methoxy group; $R^4$ is $-CH_2-CH=C(CH_3)_2$; $R^5$ is a hydroxyl group; and $R^6$ is hydrogen. This compound is glycocitrine-I (13):

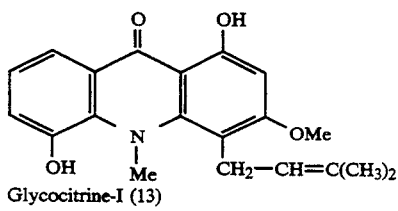
Glycocitrine-I (13)

The fourth subgroup maybe further divided to a fifth subgroup, wherein $R^5$ is a methoxy group.

In one preferred compound of this subgroup, $R^3$ is a methoxy group; $R^4$ is a methoxy group; and $R^6$ is hydrogen. This compound is 5-O,O-methyl-citrusinine-I (17):

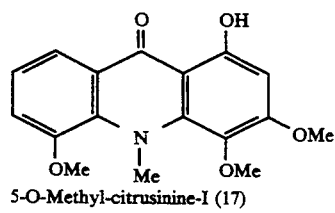
5-O-Methyl-citrusinine-I (17)

The fifth subgroup maybe further divided to a sixth subgroup, wherein $R^4$ is $-CH_2-CH=C(CH_3)_2$; and $R^6$ is a hydroxyl, methoxy or acetyl group.

In one preferred compound of this subgroup, $R^3$ and $R^6$ are methoxy groups. This compound (29)

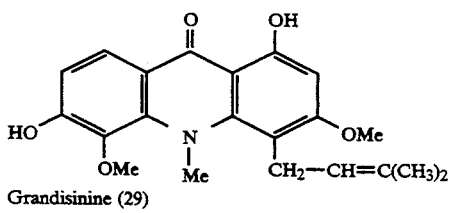
Grandisinine (29)

The sixth subgroup maybe further divided to a seventh subgroup, wherein $R^6$ is a methoxy or acetyl group.

In one preferred compound of this subgroup, $R^3$ is an acetyl group and $R^4$ is a methoxy group. This compound is 3,6-O,O-diacetyl-prenylcitpressine (28):

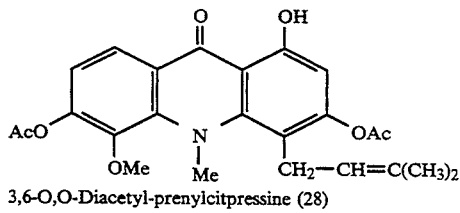
3,6-O,O-Diacetyl-prenylcitpressine (28)

In another preferred compound of this subgroup, $R^3$ and $R^4$ are methoxy groups. This compound is balyumine-B (30):

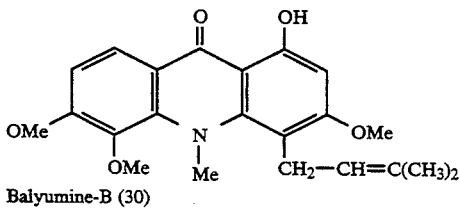
Balyumine-B (30)

Physiologically acceptable carriers, as discussed throughout the application, are to include any carrier compatible with life. The choice of carrier is readily determinable to one skilled in the art. The-physiologically acceptable carrier encompasses any of the standard carriers such as sterile solution, tablets, coated tablets and capsules. Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients. Compositions comprising such carriers are formulated by well known conventional methods. However a composition comprising the compound of the subject invention effective to inhibit growth of tumor cells is previously unknown.

Any of the above-described compositions wherein the composition comprises an agent to increase solubility represent the preferred embodiment of the invention.

Agents to increase solubility, as used throughout the application, are to include, but are not limited to compounds which react with the hydrophobic regions of the subject compounds. Some examples of suitable agents include Emulphor (a polyoxylethylated fatty acid which is water miscible and non-toxic when diluted 1:10 with either sterile water or sterile physiological saline solution) and polyvinylpyrrolidine. Both Emulphor and polyvinylpyrrolidine have been disclosed for use in administering acronycine by Svoboda, G. H. in U.S. Pat. Nos. 3,985,899, filed Oct. 12, 1976, and 4,309,431, filed Jan. 5, 1982. However, Svoboda does not teach or suggest the use of Emulphor or polyvinylpyrrolidine in the methods or compositions of the subject invention.

This invention also provides a method of inhibiting growth of tumor cells which comprises contacting the cells with a growth inhibiting amount of a compound having the structure:

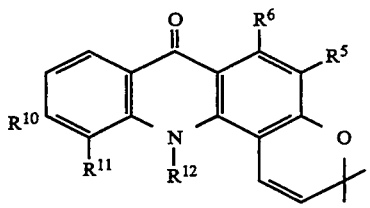

wherein $R^5$ is hydrogen or —$CH_2$—$CH$=$C(CH_3)_2$; $R^6$ is a hydroxyl group; $R^{10}$ is a hydrogen or a hydroxyl group; $R^{11}$ is a hydroxyl or methoxy group; and $R^{12}$ is a hydrogen or methyl group.

In a preferred compound of this embodiment, $R^5$ is hydrogen; $R^{10}$ is a hydroxyl group; $R^{11}$ is a methoxy group; and $R^{12}$ is a methyl group. This compound is citracridone-I (42):

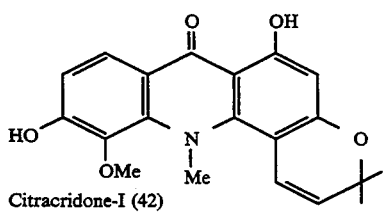

Citracridone-I (42)

The preferred embodiment may be divided to a first subgroup, wherein $R^{10}$ is a hydrogen; and $R^{11}$ is a hydroxyl group.

In a preferred compound of the first subgroup, $R^5$ is —$CH_2$—$CH$=$C(CH_3)_2$ and $R^{12}$ is hydrogen. This compound is atalaphyllinine (40):

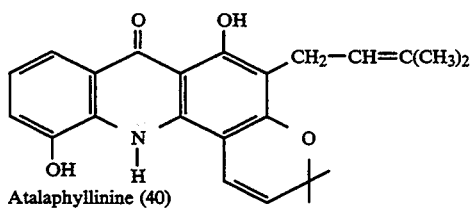

Atalaphyllinine (40)

The first subgroup may be divided to a second subgroup,
wherein $R^5$ is hydrogen.

In one preferred compound of the second subgroup, $R^{12}$ is a methyl group. This compound is 11-hydroxy-noracronycine (37);

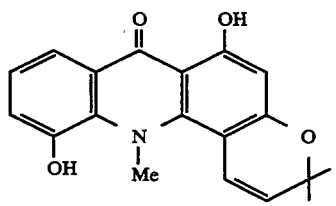

11-Hydroxy-nor-acronycine (37)

In another preferred compound of the second subgroup, $R^{12}$ is hydrogen. This compound is atalaphyllidine (34).

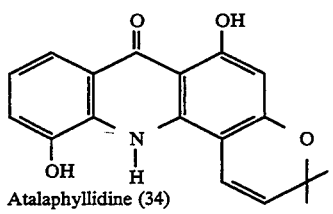

Atalaphyllidine (34)

The subjection invention further discloses a composition comprising an amount of a compound having the structure:

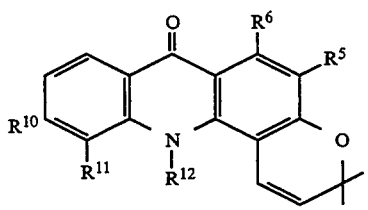

wherein $R^5$ is hydrogen or —$CH_2$—$CH$=$C(CH_3)_2$; $R^6$ is a hydroxyl group; $R^{10}$ is a hydrogen or a hydroxyl group; $R^{11}$ is a hydroxyl or methoxy group; and $R^{12}$ is a hydrogen or methyl group;
effective to inhibit growth of tumor cells and a physiologically acceptable carrier.

This invention also provides for the above-indicated compositions wherein the compound comprises hydrophilic substituents to increase solubility. Hydrophilic molecules which may be used as substituents are well known in the art. However, compositions comprising the disclosed compounds with hydrophilic substituents are previously unknown.

In the preferred embodiment, $R^6$ is a hydroxyl group; $R^{10}$ is hydrogen or a hydroxyl group; and $R^{11}$ is a hydroxyl or methoxy group.

In a preferred compound of this embodiment, $R^5$ is hydrogen; R10 is a hydroxyl group; $R^{11}$ is a methoxy group; and $R^{12}$ is a methyl group. This compound is citracridone-I (42):

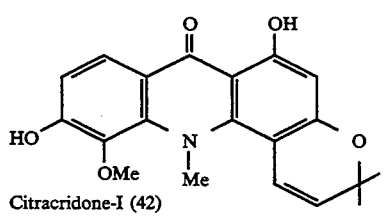

Citracridone-I (42)

The preferred embodiment may be divided to a first subgroup, wherein $R^{10}$ is a hydrogen; and $R^{11}$ is a hydroxyl group.

In a preferred compound of the first subgroup, $R^5$ is —$CH_2$—$CH$=$C(CH_3)_2$ and $R^{12}$ is hydrogen. This compound is atalaphyllinine (40):

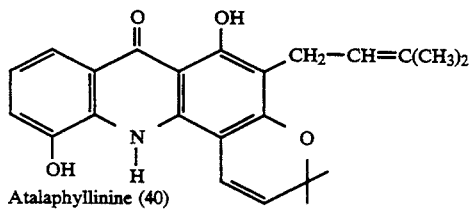

Atalaphyllinine (40)

The first subgroup may be divided to a second subgroup, wherein $R^5$ is hydrogen.

In one preferred compound of the second subgroup, $R^{12}$ is a methyl group. This compound is 11-hydroxy-noracronycine (37):

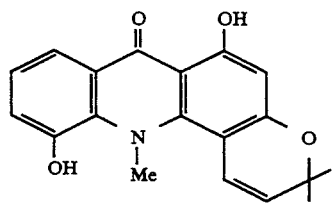

11-Hydroxy-nor-acronycine (37)

In another preferred compound of the second subgroup, $R^{12}$ is hydrogen. This compound is atalaphyllidine (34):

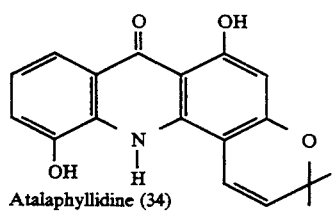

Atalaphyllidine (34)

In any of the above-defined compositions, wherein the composition comprises an agent to increase solubility, it is to be considered a preferred embodiment.

The subject invention also discloses a method of inhibiting growth of tumor cells which comprises contacting the cells with a growth inhibiting amount of a compound having the structure:

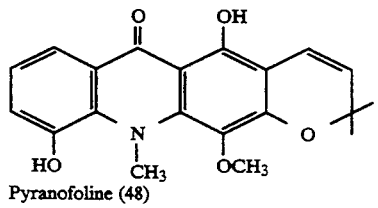

Pyranofoline (48)

Further provided is a composition comprising an amount a compound having the structure:

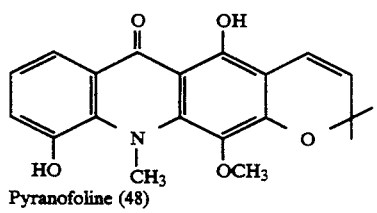

Pyranofoline (48)

effective to inhibit growth of tumor cells and a physiologically acceptable carrier.

This invention also provides for the above-indicated compositions wherein the compound comprises hydrophilic substituents to increase solubility. Hydrophilic molecules which may be used as substituents are well known in the art. However, compositions comprising the disclosed compounds with hydrophilic substituents are previously unknown.

In the preferred embodiment, the composition further comprises an agent to increase solubility.

Additionally, this invention discloses a method of inhibiting growth of tumor cells which comprises contacting the cells with a growth inhibiting amount of a compound having the structure:

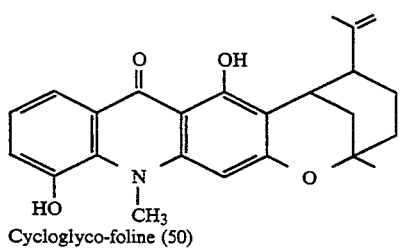

Cycloglyco-foline (50)

Also provided is a composition comprising an amount a compound having the structure:

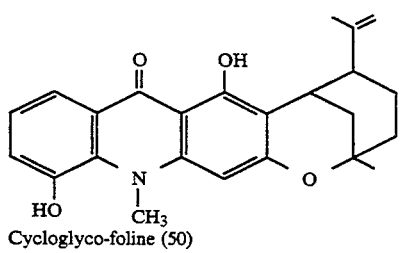

Cycloglyco-foline (50)

effective to inhibit growth of tumor cells and a physiologically acceptable carrier.

This invention also provides for the above-indicated compositions wherein the compound comprises hydrophilic substituents to increase solubility. Hydrophilic molecules which may be used as substituents are well known in the art. However, compositions comprising the disclosed compounds with hydrophilic substituents are previously unknown.

The subject invention provides a method of inhibiting growth of leukemia cells in a host in need of treatment therefor which comprises administering to the host an amount of a compound having the structure:

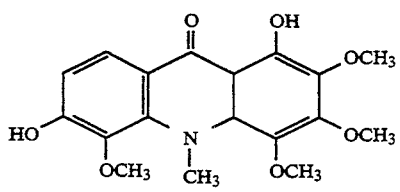

effective to inhibit growth of the leukemia cells. In a preferred embodiment, the adminstration comprises oral administration. The effective growth-inhibiting amount of the compound is typically between about 1 mg and about 500 mg. The effective growth-inhibiting amount of the compound is also typically between about 0.01 mg and about 10 mg per kg of the host's body weight. Other modes of administration are also useful, including subcutaneous injection, intraperitoneal injection, subdermal injection, intramuscular injection, and transdermal absorption.

The invention also provides a composition for inhibiting growth of leukemia cells in a host in need of treatment thereof which comprises an amount of the compound having the structure:

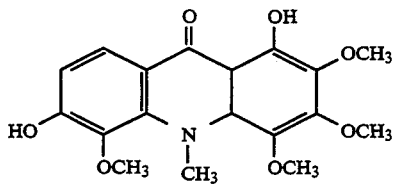

effective to inhibit growth of leukemia cells and a physiologically acceptable carrier.

The invention also provides a method of inhibiting growth of solid tumor cells in a host in need of treatment therefor which comprises administering to the host an amount of a compound having the structure:

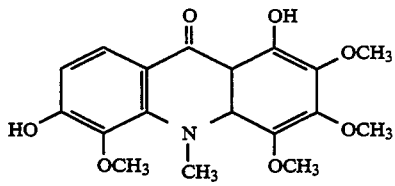

effective to inhibit growth of the solid tumor. In a preferred embodiment, the administration comprises oral administration. The effective growth-inhibiting amount of the compound is typically between about 1 mg and about 500 mg. The effective growth-inhibiting amount of the compound is also typically between about 0.01 mg and about 10 mg per kg of the host's body weight. Other modes of administration are also useful, including subcutaneous injection, intraperitoneal injection, subdermal injection, intramuscular injection, and transdermal absorption.

The invention also provides a composition for inhibiting growth of solid tumors in a host in need of treatment thereof which comprises an amount of the compound having the structure:

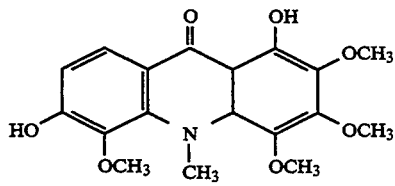

effective to inhibit growth of solid tumors and a physiologically acceptable carrier.

The following Experimental Details and Examples are set forth to aid in an understanding of the invention, and are not intended to, and should not be construed to, limit in any way the invention as set forth in the claims which follow thereafter.

EXPERIMENTAL DETAIL

All acridone alkaloids were either previously isolated from plants indigenous to Taiwan or were obtained by partial synthesis. The isolation and structure elucidation data for each compound are referenced in Tables 1-3.

The structures of compounds 4-10 have been disclosed by Wu, T. -S., Yakugaku Zasshi, 103:1103-1107 (1983); compounds 1, 11-14, 31, 33-35, 38, 39 and 48-51 have been disclosed by Wu, T. -S., J. Chem. Soc. Perkin Trans. I., 1681-1688 (1983); compounds 15-17and 27have been disclosed by Wu, T. -S. and H. Furukawa, Chem. Pharm. Bull., 31:901-906 (1983); compounds 19-21, 28, and 29have been disclosed by Wu, T. -S., C. -S. Kuoh and H. Furukawa, Phytochemistry, 22:1493-1497 (1983); compounds 22, 23, 39 and 42-45 have been disclosed by Wu, T. -S., C. -S. Kuoh and H. Furukawa, Chem. Pharm. Bull, 31:895-900 (1983); compound 25has been disclosed by Wu, T. -S., phytochemistry; 27, in press. (1988); compounds 26, 32, 36, 41, 42, 46 and 47 have been disclosed by Wu, T. -S. Kuoh and M. Furakawa, Phytochemistry, 21:1771-1773 (1982); compound 30has been disclosed by Wu, T. -S., Phytochemistry, 26:871-872 (1987); and compound 52 has been disclosed by Furukawa, H., T. -S. Wu, C. -S. Kuoh, T. Sato, Y. Nagai and K. Kagei, Chem. Pharm. Bull., 32:1647-1649 (1984).

For the precursor incorporation studies, each compound (in 0.3% dimethylsulfoxide) was preincubated with HL-60 cells (a human promyelocytic leukemic cell line) $2.2 \times 10^6$/ml, for 15 min prior to the addition of the labeled precursor (obtained from ICN Radiochemicals, Irvine, Calif.) and then incubated for 30 min. The precursors used for incorporation into DNA, RNA and protein were [$^3$H-methyl]dThd (1 $\mu$Ci, 0.15 nmole/ml), [5-$^3$H]Cyd (5 $\mu$Ci, 0.23 nmol/ml), and [2,3,4,5-$^3$H]L-Leu (0.5 $\mu$Ci, 0.004 nmol/ml), respectively. Incorporation of radioactivity in the absence of a plant compound and in the presence of dimethylsulfoxide was used as a control. The control values for incorporation into DNA, RNA and protein were 8,500, 5,600 and 1,700 cpm/$10^6$ cells, respectively. The incubation conditions and the procedures for isolating DNA, RNA and protein fractions have been previously described (Chou, T. -C., et al., Cancer Res., 43:3074-3079 (1983)) .

For growth inhibition studies, HL-60 cells ($1.5 \times 10^5$/ml) were grown in RPMI 1640 media (GIBCO, Grand Island, N.Y.) at 37° C. in humidified 5% $CO_2$ for 72 h. Viable cells were determined using trypan blue exclusion and counted in a hemocytometer. The fractional inhibition for each compound concentration (0.0025-0.05 mg/ml in 0.1% dimethylsulfoxide) was analyzed with the median-effect plot using a computer program (Chou, T. -C and P. Talalay, Adv. Enzyme Regul., 22:27-55 (1984); Chou, J. and T. -C. thou, Dose-Effect analysis with microcomputers: Quantitation of ED50, LD50, synergism, antagonism, low-dose risk, receptor ligand binding and enzyme kinetics. A computer software disk for Apple II series or IBM-PC and manual. Elsevier Science Publishers, Elsevier-BioSoft, Cambridge, United Kingdom (1986)). The median-effect concentration (IC$_{50}$) was determined automatically for three to five dose-effect levels. Cell growth in the absence of plant compound and in the presence of dimethylsulfoxide was used as a control. Dimethylsulfoxide alone inhibited cell growth 3.9%±1.5% during the 72 h incubation period. Those data with negative values represent activations.

Results and Discussion

Effects of Acridine Alkaloids on Precursor Incorporation into Cellular DNA

Human promyelocytic cells (HL-60) were incubated with [$^3$H-methyl]dTHD in the presence and absence of a plant alkaloid. The percentage of inhibition of precursor incorporation in to DNA was tested with compound concentration of 0.03 mg/ml.

Acridin-9-one derivatives (Table 1), which bear 1,3-di (4 and 5) and 1,3,10-tri-sustituents (6–10) showed no significant activity on the inhibition of DNA synthesis with the exception of compound 10 which exhibited excellent inhibitory effect by inhibiting over 90% of DNA synthesis. Glycocitrine-II (11) is a potent inhibitor of cell DNA synthesis, while its 3-methyl derivative (12) shows only moderate inhibitory activity.

TABLE 1

Inhibition of macromolecule biosynthesis and HL-60 cell growth by acridin-9-one derivatives

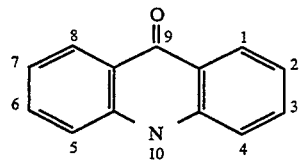

| No. | | Position 1 | 2 | 3 | 4 | 5 | 6 | 10 | Molecular Weight | % Inhibition of Precursor Incorporation at 0.03 mg/mL DNA | RNA | Protein | Cell Growth Inhibition, IC$_{50}$ (mg/mL) | ($\mu$M) |
|---|---|---|---|---|---|---|---|---|---|---|---|---|---|---|
| 4 | 1,3-Dihydroxy-acridone | OH | | OH | | | | H | 227.26 | 76.7 | 50.6 | 62.8 | 0.0206 | 90.7 |
| 5 | 1,3-O,O-Diacetyl-acridone | OAc | | OAc | | | | H | 311.34 | 39.7 | 24.9 | 26.9 | >0.04 | >129 |
| 6 | 1,3-Diacetyl-N-methyl acridone | OAc | | OAc | | | | Me | 325.36 | 23.0 | 2.7 | −12.8 | >0.04 | >123 |
| 7 | 1-Hydroxy-3-methoxy N-methyl acridone | OH | | OMe | | | | Me | 255.30 | 48.4 | 39.5 | 25.2 | >0.04 | >157 |
| 8 | 1-Methoxy-3-Hydroxy N-methyl acridone | OMe | | OH | | | | Me | 255.30 | 53.3 | 51.2 | 25.7 | >0.04 | >157 |
| 9 | 3-O-Acetyl-1-methoxy-R-methyl acridone | OMe | | OAc | | | | Me | 297.34 | 71.1 | 61.6 | 30.0 | 0.0305 | 102.6 |
| 10 | 1,3-Dimethoxy-N-methyl acridone | OMe | | OMe | | | | Me | 269.32 | 91.2 | 65.8 | 64.4 | 0.0092 | 34.2 |
| 11 | Glycocitrine-II | OH | | OH | R | | | Me | 309.38 | 99.5 | 97.1 | 95.3 | 0.0082 | 26.5 |
| 12 | 3-O-methyl-glycocitrine-II | OH | | OMe | R | | | Me | 323.40 | 61.8 | 53.8 | 50.3 | >0.04 | >124 |
| 13 | Glycocitrine-I | H | | OMe | R | OH | | Me | 339.40 | 97.5 | 43.9 | 41.1 | 0.0014 | 4.1 |
| 14 | O—O-Diacetyl-glycocitrine-I | OAc | | OMe | R | OAc | | Me | 423.48 | 94.7 | 63.8 | 89.8 | 0.0056 | 13.2 |
| 15 | Citrusinine-II | OH | | OH | OMe | OH | | Me | 287.30 | 88.5 | 91.7 | 54.3 | 0.017 | 59.2 |
| 16 | Citrusinine-I | OH | | OMe | OMe | OH | | Me | 301.32 | 97.0 | 96.5 | 87.0 | 0.0026 | 8.6 |
| 17 | 5-O-Methyl-citrusinine-I | OH | | OMe | OMe | OMe | | Me | 315.34 | 93.4 | 96.4 | 93.0 | 0.0027 | 8.6 |
| 18 | 1,3,4,5-Tetra-methoxy-N-methyl acridone | OMe | | OMe | OMe | OMe | | Me | 329.36 | 91.5 | 57.0 | 71.8 | 0.0133 | 40.4 |
| 19 | Grandisine-II | OH | | OH | | OMe | OMe | Me | 301.32 | 76.5 | 96.0 | 27.3 | >0.04 | >133 |
| 20 | O-Acetyl-grandisine-II | OH | | OAc | | OMe | OMe | Me | 343.36 | 24.4 | 77.0 | −5.6 | 0.0387 | 112.7 |
| 21 | Grandisine-I | OH | | OMe | | OH | OMe | Me | 301.32 | 71.7 | 69.5 | 22.8 | >0.04 | >133 |
| 22 | Citpressine-I | OH | | OMe | | OMe | OMe | Me | 301.32 | 65.0 | 80.9 | 90.5 | >0.04 | >133 |
| 23 | Citpressine-II | OH | | OMe | | OMe | OMe | Me | 315.34 | 34.8 | 95.0 | 28.3 | >0.04 | >127 |
| 24 | 1-O-Methyl-citpressine-II | OMe | | OMe | | OMe | OMe | Me | 329.36 | 93.1 | 67.3 | 75.6 | 0.022 | 66.8 |
| 25 | Buntanine | OH | R | OH | | OMe | OH | Me | 355.40 | 96.6 | 29.8 | 40.1 | 0.0036 | 10.1 |
| 26 | N-methyl-atalaphylline | OH | R | OH | R | OH | | Me | 393.48 | 99.6 | 28.2 | 44.3 | 0.0054 | 13.7 |
| 27 | Prenylcitpressine | OH | | OH | R | OMe | OH | Me | 355.40 | 52.4 | 21.1 | −15.7 | 0.036 | 94.5 |
| 28 | 3,6-O,O-Diacetyl-prenylcitpressine | OH | | OAc | R | OMe | OAc | Me | 439.48 | 96.8 | 96.1 | 89.6 | 0.0022 | 5.0 |
| 29 | Grandisinine | OH | | OMe | R | OMe | OH | Me | 355.42 | 98.5 | 96.5 | 94.6 | 0.006 | 16.9 |
| 30 | Balyumine-B | OH | | OMe | R | OMe | OMe | Me | 383.44 | 86.9 | 92.5 | 87.0 | 0.0017 | 4.4 |
| 31 | Glyfoline | OH | OMe | OMe | OMe | OMe | OH | Me | 361.36 | 93.5 | 65.7 | 90.7 | 0.0004 | 1.1 |

Where R = —CH$_2$—CH=C(CH$_3$)$_2$

Compounds with penta-substituents split into two categories; those with substitution at position 4 (13–18) display excellent activity, whereas others possessing a substituent at position 6 (19–24) show relatively weaker activity. The only exception is compound 24 which inhibits 93% of DNA synthesis. In general, polysubstituted acridine-9-ones (25–31) inhibit DNA synthesis.

In the series of acronycine derivatives (Table 2), 6-hyroxypyrano[2,3-c]acridine-7-one (32) did not show good activity in this study, while the inhibitory activity of its O-methylated product (33) was markedly increased. Acronycine (1) was found to inhibit about 90% of prelabeled precursor incorporation into DNA, while poor activity for its disubstituted analogs (34–36) was observed. With the exception of compound 41 which has no substituent at C-11, trisubstituted acronycine potency as their parent compounds, 37 and 42, respectively.

Both derivatives of pyrano[3,2-b]acridine-6-one (48 and 49) and their analog, cycloglycofoline (50) inhibited DNA synthesis significantly, whereas furofoline derivative 51 and acridine dimer (52) were not active (Table 3).

TABLE 3

Inhibition of macromolecule biosynthesis and HL-60 cell growth by pyranofoline and furofoline derivatives

| No. | | Molecular Weight | % Inhibition of Precursor Incorporation at 0.03 mg/mL | | | Cell Growth Inhibition, $IC_{50}$ | |
|---|---|---|---|---|---|---|---|
| | | | | | | (mg/mL) | (μM) |
| 48 | Pyranofoline | 353.40 | 98.8 | 97.2 | 96.4 | 0.0031 | 8.8 |
| 49 | Methoxymethyl-pyranofoline | 397.44 | 85.3 | 70.1 | 87.3 | 0.0187 | 47.1 |
| 50 | Cycloglycofoline | 391.48 | 98.7 | 55.7 | 92.1 | 0.0058 | 14.8 |
| 51 | Furofoline-II | 322.38 | 13.1 | −46.3 | 19.5 | >0.04 | >124.1 |
| 52 | Glycobismine-A | 602.74 | −27.8 | −57.4 | −13.2 | >0.04 | >66.4 | derivatives (37–40) showed potent inhibitory effects on DNA synthesis.

Effect of Acridine Alkaloids on the Labeled Precursor Incorporation into RNA and Protein

TABLE 2

Inhibition of macromolecule biosynthesis and HL-60 cell growth by acronycine derivatives

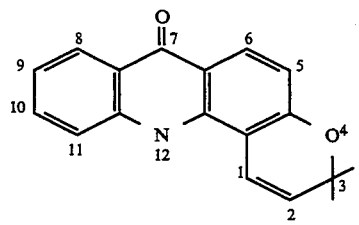

| No. | | Position | | | | | Molecular Weight | % Inhibition of Precursor Incorporation at 0.03 mg/mL | | | Cell Growth Inhibition, $IC_{50}$ | |
|---|---|---|---|---|---|---|---|---|---|---|---|---|
| | | 5 | 6 | 10 | 11 | 12 | | DNA | RNA | Protein | (mg/mL) | (μM) |
| 32 | des-N-methyl-nor-acronycine | | OH | | | H | 293.36 | 69.2 | 77.5 | 85.9 | 0.0091 | 31.0 |
| 33 | des-N-methyl acronycine | | OMe | | | H | 307.38 | 93.8 | 67.3 | 86.4 | 0.0054 | 17.6 |
| 34 | Atalaphyllidine | | OH | | OH | H | 309.36 | 78.9 | 94.8 | 82.9 | 0.0013 | 4.2 |
| 35 | Noracronycine | | OH | | | Me | 307.38 | 25.5 | 94.0 | 4.7 | >0.04 | >130 |
| 1 | Acronycine | | OMe | | | Me | 293.36 | 91.4 | 21.3 | 25.4 | 0.0077 | 26.2 |
| 36 | Severifoline | R | OH | | | H | 361.46 | 20.0 | ND | ND | >0.04 | >111 |
| 37 | 11-Hydroxy-noracronycine | | OH | | OH | Me | 323.38 | 98.6 | 96.6 | 95.3 | 0.0023 | 7.1 |
| 38 | 1,2-Dihydro-11-hydroxy-nor acronycine | | OH | | OH | Me | 325.38 | 98.8 | 76.6 | 92.2 | 0.0055 | 16.9 |
| 39 | 11-methoxy-noracronycine | | OMe | | OMe | Me | 337.40 | 98.9 | 39.9 | 36.2 | 0.0058 | 17.2 |
| 40 | Atalaphyllinine | R | OH | | OH | H | 377.46 | 98.8 | 24.4 | 41.8 | 0.0012 | 3.2 |
| 41 | N-Methylseverifoline | R | OH | | | Me | 375.48 | 21.3 | −17.9 | 13.2 | >0.04 | >107 |
| 42 | Citracridone-I | | OH | OH | OMe | Me | 353.40 | 98.5 | 96.9 | 90.5 | 0.0029 | 8.2 |
| 43 | 1,2-dihydrocitracridone-I | | OH | OH | OMe | Me | 355.40 | 94.9 | 68.0 | 81.9 | 0.0064 | 18.0 |
| 44 | Citracridone-II | | OH | OMe | OMe | Me | 367.42 | 77.6 | 96.4 | 62.7 | >0.04 | >109 |
| 45 | 6-O-Methylcitracridone-II | | OMe | OMe | OMe | Me | 381.44 | 98.7 | 37.8 | 49.8 | 0.0059 | 15.5 |
| 46 | 11-Hydroxy-N-methyl severifoline | R | OH | | OH | Me | 391.48 | 97.9 | 16.7 | 4.22 | 0.0059 | 15.1 |
| 47 | 11-O-Acetyl-N-methyl severifoline | R | OH | | OAc | Me | 433.52 | 58.4 | 16.2 | 36.2 | 0.0088 | 20.3 |

Where R = —$CH_2$—CH=$C(CH_3)_2$

In comparing atalaphyllidine (34) with atalaphyllinine (40), the latter showed greater activity. Thus, addition of a 3-methyl-2-butenyl side-chain at the C-5 position of 34 results in increased activity. However, addition of this side-chain at the same position in noracronycine (35) had no effect on the inhibitory activity of 41. Compounds with four substituents at 6, 10, 11 and 12 (42–45), and 5, 6, 11 and 12 (46) also exhibited significant activity. It should also be noted here that 1,2-dihydro derivatives 38 and 43 were shown to have the same HL-60 cells were incubated with [5-$^3$H]Cyd or [2,3,4,5-$^3$H]L-Leu in the presence and absence of alkaloids (0.03 mg/ml) in order to find the effects of the alkaloid on the incorporation of labeled precursors into RNA or protein. Most acridine alkaloids were found to have either a moderate or low inhibitory effect on RNA and protein biosynthesis. Over 90% of RNA and protein biosynthesis were inhibited by compounds 11, 16, 17, 22, 28, 29 and 30 (Table 1). The same results were obtained from some derivatives of acronycine (Table 2) and pyranofoline derivative (50, Table 3). In most cases, the amount required to inhibit precursor incorporation into DNA was less than that to inhibit precursor incorporation into RNA or protein (i.e. DNA synthesis is inhibited most potently).

Effect of Acridine Alkaloids on the growth of Leukemic HL-60 Cells

The plant alkaloids were further examined for their effects on cell growth inhibition (Tables 1–3).

Compounds listed in Table 1 (acridin-9-one derivatives) with substituents at 1, 3 and 10 (4–9) and 1, 3, 5, 6 and 10 (19–24), in general, did not inhibit cell growth synthesis, r=0.43, (n=35). It appears that DNA synthesis is the major target for this group of compounds.

In summary, acronycine (1) has been shown to have a broad spectrum of antitumor activity against experimental neoplasms in laboratory animals (Table 4). In an attempt to search for more potent compounds and to determine structure-activity relationships, 50 acronycine-related acridine alkaloids were examined for their effects on inhibition of precursor incorporation into DNA, RNA and protein as well as their potency on inhibition of leukemic HL-60 cell growth.

TABLE 4

Experimental Tumor Spectrum of Acronycine (Svoboda et al.)

| Tumor | Dose (ip, mg/kg/day) | Average weight change (g. T/C) | Average life span (days, T/C) | Percent activity |
|---|---|---|---|---|
| B82 leukemia | 37.5 × 1 × 7 | −1.4/+0.4 | 23.7/14.6 | 61 |
| C1498 leukemia | 28 × 1 × 10 | −1.4/+0.8 | 31.5/17.6 | 79(7) |
| P1534 leukemia | 30 × 1 × 10 | −0.2/−0.7 | 16.5/18.2 | 0 |
| L5178Y leukemia | 28 × 1 × 10 | +2.2/+3.2 | 24.2/15.0 | 62 |
| AKR leukemia | 28 × 1 × 10 | +0.1/+0.8 | 38.3/21.5 | 78(5) |
| Ehrlich ascites | 30 × 1 × 10 | +5.6/+7.8 | 21.8/18.4 | 0(1) |
| | | | Average tumor size (mm, T/C) | |
| Sarcoma 180 | 30 × 1 × 10 | +3.2/+6.0 | 7.1/11.9 | 40(9) |
| Mecca lymphosarcoma | 30 × 1 × 10 | −0.4/+2.5 | 6.2/16.9 | 63(7) |
| Ridgeway osteogenic sarcoma | 48 × 1 × 9 | −0.6/+3.4 | 0/9.6 | 100(10) |
| X5563 myeloma | 30 × 1 × 8 | +0.1/+0.3 | 0/9.1 | 100(8) |
| Adrenocarcinoma 755 | 30 × 1 × 10 | −0.5/+1.9 | 11.9/19.7 | 40(10) |
| Shionogi carcinoma 115 | 36 × 1 × 9 | +1.4/+1.4 | 0/15.3 | 100(7) |
| S91 melanoma | 36 × 1 × 9 | −1.4/+0.1 | 0/14.1 | 100(4) |

(with the exception of compound 10). Most compounds bearing substituents at the 1, 3, 4, 5 and 10 positions (13–17, 26–31) showed significant inhibition. The most potent compound in this series was glyfoline (31) with an $IC_{50}$ of 0.0004 mg/ml (1.11 μM).

Cell growth inhibition by pyrano[2,3-c]acridine-7-one derivatives was compared to acronycine (1) (Chou, T. -C., et al., Cancer Res. 43:3074–3079 (1983)) (Table 2). The simple 6-hydroxyl substituted derivatives (32, 35 and 41) only showed moderate cell growth inhibitory activity but their O-methylated counterparts (33, 1 and 45, respectively) were found to be significantly active. Atalaphyllidine (34) and its substituted 2-(3-methyl-2-butenyl) or N-methyl derivatives (40 and 37) were shown to have comparable activity. Severifoline (36) was reported to have no antitumor activity, but the antitumor activity was induced significantly by introduction of an OH group at position 11 (40). A similar trend was observed on several pairs of compounds (32 vs. 34; 35 vs. 37; 41 vs. 46). The 1,2-dihydro derivatives (38 and 43) were found to be only half as potent as their parent compounds (37 and 42, respectively). A linear isomer of acronycine, pyranofoline (48) (Table 3) and its analog cycloglycofoline exhibited better activity than that of acronycine. It is also interesting to note that, in general, there is a correlation between the potency of inhibiting precursor incorporation into DNA and the potency of inhibiting cell growth among these analogs. The correlation coefficient (r) for percent inhibition of DNA synthesis (x) vs log ($IC_{50}$ in mg/ml) for HL-60 cell growth (y) was r=0.54, whereas similar plots for RNA synthesis gave r-0.18 and for protein In general, derivatives of acronycine (Pyrano[2,3-c]acridin-7-one) (Table 2) exhibited the most potent inhibition on the growth of leukemic ML-60 cells. It has also been found that acridin-9-one derivatives (Table 1) with sustituents at the 1, 3, 4 and 10 positions (13, 14, 16, 17, 26, 28, 29 and 31) had significant activity against leukemic cells in vitro. There are structural similarities between these compounds and acronycine; the latter is considered as a 1, 3, 4 and 10 tetra-substituted acridin-9-one derivative. Accordingly, substituents at the above four positions of the acridin-9one ring system may be essential for optimum biological activity.

The above structure-activity relationships may provide useful directions for future synthetic approaches to developing new antitumor chemotherapeutic agents.

Summary of In Vivo Preliminary Studies on Acridones (Tables 5–7)

A. L1210 Leukemia (Natural products used)

Compound 31 (SK 32889, TSA-35, glyfoline) showed some activity against L1210 leukemia in BDF mice at a low dose (12.5 mg/kg, starting day 1 for 4 days, i.p. injection)

Compound 34 (TSA-36) also showed evidence of antileukemic activity.

Compound 37 (TSA-7) and compound 17 (TSA-15) were not active.

B. Lewis Lung Carcinoma (Synthetic compounds used)

Compound 31 a=25 and 50 mg/kg daily for 4 days i.p. injection to C57BL/6 mice showed less toxicity to mice than that of compound 1 (acronycine, TSA-33, SK 32121). At 25 and 50 mg/kg, compound 31 increased life-span by 42% and >92%, respectively, whereas compound increased life-span by 40% and 40%, respectively.

There were 2 out of 5 long-term survivals for 50 mg/kg for compound 31. Other groups had no long term survivals.

Carcinoma E07713 (Synthetic compounds used)

At 100 mg/kg daily for 4 days i.p. compound 1 showed 1 out of 3 toxicity induced deaths but no deaths were observed as a consequence of administration of compound 31.

At 50 mg/kg and 100mg/kg, compound 31 increased life-span by 17% and >39%, respectively, whereas compound 1 increased life-span by 26% and 4% (although toxic), respectively.

TABLE 5

Survival Time Evaluation
Tumor-Lewis Lung C. 3 × 10⁵ cells (ip) in C57BL/6, FEM, 19-21 g
Drug: A = SK 32121 TSA-33 (acronycine)
B = SK 32089 TSA-35 (glyfoline)
Diluent-CMC + 1 drop Tween 80    Schedule: Day 1, QDX4 (ip)

| # | Dose MG/KG | | Day #7 AWC (g) | Survival Time | | | | | | | | | AST+ | % ILS* | N/T |
|---|---|---|---|---|---|---|---|---|---|---|---|---|---|---|---|
| 1 | CONTROL | | +0.1 | 10 | 10 | 10 | 10 | 10 | 10 | 10 | 11 | 11 | 12 | 10.4 | | 0/10 |
| 2 | Acronycin | 50 | −0.8 | 14 | 14 | 15 | 15 | 15 | | | | | | 14.6 | 40 | 0/5 |
| 3 | Acronycin | 25 | −0.6 | 14 | 14 | 14 | 14 | 17 | | | | | | 14.6 | 40 | 0/5 |
| 4 | TSA-35 | 50 | +0.2 | 14 | 14 | 14 | >29 | >29 | | | | | | >20 | >92 | 2/5 |
| 5 | TSA-35 | 25 | +0.2 | 14 | 14 | 14 | 14 | 18 | | | | | | 14.8 | 42 | 0/5 |

*Increase in lifespan of 25% or greater indicates activity. Mice dying of toxicity (t) not included in AST evaluation. N/T = number of 29 day survivors/total mice.
Average weight change. Changes of less than 1 gm are not considered significant. Tumor may contribute to the body weight. Toxicity decreases body weight.
+Average survival time.

TABLE 6

Survival Time Evaluation
Tumor-Carcinoma EO771 3 × 10⁵ cells (ip) in C57BL/6, FEM, 19-21 g
Drug: A = SK 32121 TSA-33 (acronycine)
B = SK 32089 TSA-35 (glyfoline)
Diluent-CMC + 1 drop Tween 80    Schedule: Day 1, QDX4 (ip)

| # | Dose MG/KG | | Day #7 AWC (g) | Survival Time | | | | | AST+ | % ILS* | N/T |
|---|---|---|---|---|---|---|---|---|---|---|---|
| 1 | CONTROL | | +1.4 | 10 | 10 | 10 | 11 | 12 | 10.6 | | 0/5 |
| 2 | Acronycin | 100 | +0.5 | 4t | 10 | 12 | | | 11.0 | 4 | 0/3 |
| 3 | Acronycin | 50 | +0.4 | 11 | 11 | 14 | 14 | 17 | 13.4 | 26 | 0/5 |
| 4 | TSA-35 | 100 | +0.3 | 11 | 11 | >22 | | | >15 | >39 | 1/3 |
| 5 | TSA-35 | 50 | +0.6 | 10 | 11 | 12 | 14 | 15 | 12.4 | 17 | 0/5 |

*Increase in lifespan of 25% or greater indicates activity. Mice dying of toxicity (t) not included in AST evaluation. N/T = number of 22 day survivors/total mice.
Average weight change. Changes of less than 1 gm are not considered significant. Tumor may contribute to the body weight. Toxicity decreases body weight.
+Average survival time.

TABLE 7

Survival Time Evaluation
Tumor-L1210 10⁶ cells (ip) in BDF1 (female) 19-21 g
Drug: A = SK 32887 TSA-7
B = SK 32888 TSA-15    Diluent-DMSO, 0.05 ml/m
C = SK 32889 TSA-35    Schedule: Day 1, QDX4 (ip)

| # | | Dose@ MG/KG | Day 6 AWC (g) | Survival Time | | | | | MST | % ILS* | N/T |
|---|---|---|---|---|---|---|---|---|---|---|---|
| 1 | Control (DMSO) | | +2.6 | 7 | 7 | 7 | 7 | 7 | 7.0 | | 0/5 |
| 2 | SK 32887 11-Hydroxy-nor-acronycine (37) TSA-7 | 6.25 | +2.0 | 7 | 7 | | | | 7.0 | 0 | 0/2 |
| 3 | SK 32887 11-Hydroxy-nor-acronycine (37) TSA-7 | 25 | +1.8 | 7 | 7 | | | | 7.0 | 0 | 0/2 |
| 4 | SK 32888 5-O-Methyl-citrusinine-I (17) TAS-15 | 6.25 | +1.8 | 7 | 7 | | | | 7.0 | 0 | 0/2 |
| 5 | SK 32888 5-O-Methyl-citrusinine-I (17) TSA-15 | 12.5 | +1.5 | 7 | 7 | | | | 7.0 | 0 | 0/2 |
| 6 | SK 32889 Glyfoline (31) TSA-35 | 6.25 | +1.8 | 7 | 7 | | | | 7.0 | 0 | 0/2 |
| 7 | SK 32889 Glyfoline (31) | 12.5 | +2.0 | 8 | 8 | | | | 8.0 | 14 | 0/2 |

TABLE 7-continued

| | | | | | | | | |
|---|---|---|---|---|---|---|---|---|
| | TSA-35 | | | | | | | |
| 1 | SK 32090 Atalaphyllidine (34) TSA-36 | 6.25 | +1.7 | 7 | 7 | 7.0 | 0 | 0/2 |
| 2 | SK 32090 Atalaphyllidine (34) TSA-36 | 25. | +1.5 | 7 | 8 | 7.5 | 7 | 0/2 |
| 3 | Sk 32091 Cycloglycofoline (50) TSA-40 | 12.5 | +1.8 | 8 | 9 | 8.5 | 21 | 0/2 |

*Increase in lifespan of 25% or greater indicates activity. Mice dying of toxicity (t) not included in MST evaluation. N/T = Number of nine day survivors/total mice.
@Low doses had been used for testing.

TABLE 8

Chemotherapeutic Effects of Acronycine and TSA-35 against Solid Tumors in Mice

| Compounds | Dose (mg/kg, ip Day 1 QDX4) | Lewis Lung Carcinoma | | | E07713 Mammary Adenocarcinoma | | | B-16 Melanoma | | |
|---|---|---|---|---|---|---|---|---|---|---|
| | | Day 7 BWC** (g) | % ILS* | N/T | Day 7 BWC (g) | % ILS | N/T | Day 7 BWC (g) | % ILS | N/T |
| Acronycine | 0 | +0.6 | NA | 0/30 | +1.4 | NA | 0/5 | +0.8 | NA | 0/5 |
| | 25 | −0.6 | 40 | 0/5 | — | — | — | — | — | — |
| | 50 | −0.5 | 34 | 0/15 | +0.4 | 26 | 0/5 | −0.6 | 24 | 0/5 |
| | 100 | 5/5 death | NA | 0/5 | 1/3 death | 4 | 0/3 | — | — | — |
| TSA-35 (glyfoline) | 25 | +0.2 | 42 | 0/5 | +0.6 | 17 | 0/5 | +0.2 | 31 | 0/5 |
| | 50 | +0.3 | >59 | 2/15 | +0.3 | >95 | 1/3 | +0.4 | 40 | 0/5 |
| | 100 | +0.5 | >46 | 1/10 | — | — | — | — | — | — |
| | 150 | −0.3 | >79 | 2/8 | — | — | — | −1.0 | >56 | 1/5 |

*Percent increase in life-span
**Body weight change
Number of 40-day tumor-free mice/total number of mice bearing tumor

TABLE 9

Cross-Resistance Studies
RELATIVE POTENCY OF INHIBITING CELL GROWTH BY GLYFOLINE IN DOXORUBICINE SENSITIVE (L1210/O) AND RESISTANT (L1210/Dx) CELLS

| Cell Line | Glyfoline $IC_{50}$ ($\mu M$) | Doxorubicin $IC_{50}$ ($\mu M$) | m-AMSA $IC_{50}$ ($\mu M$) |
|---|---|---|---|
| L1210/0 | 2.09 | 0.028 | 0.0001–0.001 |
| L1210/Dx | 3.31 | 0.73 | 0.061 |
| ($IC_{50}$) 0/($IC_{50}$) Dx | 1.58 | 26.1 | 61–610 |

Cross-resistance studies

L1210 cell line resistant to doxorubicin (L1210/Dx) with 26-fold increase in $IC_{50}$ toward doxorubicin and 6-fold resistant to m-AMSA when compared with the parent cell line (L1210/0) was used for cross-resistance studies. The $IC_{50}$'s of glyfoline was 2.09 $\mu M$ for L1210/0 and 3.31 $\mu M$ for L1210/Dx which showed only 1.6-fold differences suggesting very little cross-resistance toward glyfoline.

TABLE 10

SURVIVAL TIME EVALUATION
0.2 ML BREI (ip) ca. 10 6 cells IN BDF1 (FEMALE) 19–21 g
DRUG - A = GLYFOLINE
DILUENT - COCKTAIL DIL 1:10 dextrose
SCHEDULE - DAY 1, QDX4 bid (ip) DAY 1, QDX4 per os

| | DOSE MG/KG | DAY 7 AWC (g) | SURVIVAL TIME | | | | | AST | % ILS | N/T |
|---|---|---|---|---|---|---|---|---|---|---|
| 1 | CONTROL | +1.4 | 11 | 11 | 12 | 13 | 13 | 12.0 | | 0/5 |
| 1 | GLYF 100 bid | +1.0 | 13 | 13 | 14 | 14 | 17 | 14.2 | 18 | 0/5 |
| 3. | GLYF 500 p.o. | +0.8 | 13 | 14 | 15 | 15 | >40 | >19 | >62 | 1/5 |

*INCREASE IN LIFESPAN OF 25% OR GREATER INDICATES ACTIVITY
Mice dying of toxicity (t) not included in AST evaluation.
M/T = NUMBER OF 15 DAY SURVIVORS/TOTAL MICE
COCKTAIL = CITRIC AC + BENZYL ALC + TWEEN80 + PB0300 + ABS ETHANOL
Oral route: one tumor-free survival for >40 days.

What is claimed is:

1. A method of inhibiting growth of leukemia cells in a host in need of treatment therefor which comprises administering to the host an amount of a compound having the structure:

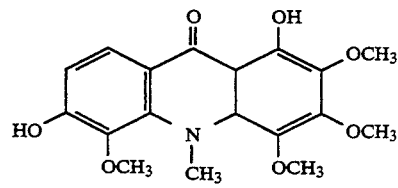

which is effective to inhibit growth of the leukemia cells.

2. The method of claim 1, wherein the administration comprises oral administration.

3. The method of claim 1, wherein the effective growth-inhibiting amount of the compound is between about 1 mg and about 500 mg.

4. The method of claim 1, wherein the effective growth-inhibiting amount of the compound is between about 0.01 mg and about 10 mg per kg of the host's body weight.

5. A method of inhibiting growth of solid tumor cells in a host in need of treatment therefor which comprises administering to the host an amount of a compound having the structure:

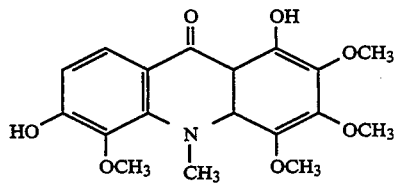

6. The method of claim 5, wherein the administration comprises oral administration.

7. The method of claim 5, wherein the effective growth-inhibiting amount of the compound is between about 1 mg and about 500 mg.

8. The method of claim 5, wherein the effective growth-inhibiting amount of the compound is between about 0.01 mg and about 10 mg per kg of the host's body weight.

* * * * *